US012584897B2

(12) United States Patent
Weich

(10) Patent No.: US 12,584,897 B2
(45) Date of Patent: Mar. 24, 2026

(54) GAS DETECTION DEVICE AND GAS DETECTION PROCESS, WHICH GENERATE A WARNING AND AN ALARM

(71) Applicant: Drager Safety AG & Co. KGaA, Lübeck (DE)

(72) Inventor: Rüdiger Weich, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 118 days.

(21) Appl. No.: 18/659,105

(22) Filed: May 9, 2024

(65) Prior Publication Data

US 2024/0385162 A1 Nov. 21, 2024

(30) Foreign Application Priority Data

May 15, 2023 (DE) ..................... 10 2023 112 716.0

(51) Int. Cl.
G08B 21/14 (2006.01)
G01N 33/00 (2006.01)
G08B 21/12 (2006.01)

(52) U.S. Cl.
CPC ..... G01N 33/0065 (2013.01); G01N 33/0068 (2024.05); G08B 21/12 (2013.01)

(58) Field of Classification Search
None
See application file for complete search history.

(56) References Cited

U.S. PATENT DOCUMENTS

| | | | |
|---|---|---|---|
| 4,231,249 A | 11/1980 | Zuckerman | |
| 4,384,283 A | 5/1983 | Drope et al. | |
| 10,386,258 B1 * | 8/2019 | Steele | G01M 3/22 |

(Continued)

FOREIGN PATENT DOCUMENTS

| | | |
|---|---|---|
| CN | 103018281 A | 4/2013 |
| CN | 107402285 A | 11/2017 |

(Continued)

*Primary Examiner* — John F Mortell
(74) *Attorney, Agent, or Firm* — McGlew and Tuttle, P.C.

(57) ABSTRACT

A gas detection device and a gas detection process are capable of detecting a target gas. The sensor unit measures the target gas concentration and generates a target gas signal (con), which includes a temporal sequence of target gas signal values. If a target gas signal value is between a lower target gas threshold ($con_{low}$) and a higher target gas threshold, a target gas warning is issued. If the target gas signal value is greater than the greater target gas threshold, a target gas warning is issued. In addition, an aggregation signal (STEV, TWA) is generated, which is an averaging or accumulation of several target gas signal values. If an aggregated value is between a smaller and a larger aggregation threshold ($STEV_{low}$, $TWA_{low}$, $STEV_{high}$, $TWA_{high}$), an aggregation warning is issued. If the aggregated value is greater than the larger aggregation threshold ($STEV_{high}$, $TWA_{high}$), an aggregation alarm is issued.

10 Claims, 3 Drawing Sheets

(56)                    References Cited

U.S. PATENT DOCUMENTS

| | | | |
|---|---|---|---|
| 2017/0169692 A1 | 6/2017 | Parra et al. | |
| 2021/0077836 A1 | 3/2021 | Ferraro et al. | |
| 2021/0086169 A1* | 3/2021 | Ushigome | B01J 27/122 |
| 2022/0335817 A1* | 10/2022 | Schober | G06N 3/0499 |

FOREIGN PATENT DOCUMENTS

| | | |
|---|---|---|
| CN | 113958368 A | 1/2022 |
| CN | 114295737 A | 4/2022 |
| CN | 115099637 A | 9/2022 |
| EP | 2639580 A1 | 9/2013 |
| JP | 2015011520 A | 1/2015 |
| JP | 2021174228 A | 11/2021 |
| SE | 522712 C2 | 3/2004 |
| WO | 0186260 A1 | 11/2001 |

* cited by examiner

GAS DETECTION DEVICE AND GAS DETECTION PROCESS, WHICH GENERATE A WARNING AND AN ALARM

CROSS REFERENCE TO RELATED APPLICATIONS

This application claims the benefit of priority under 35 U.S.C. § 119 of German Application 10 2023 112 716.0, filed May 15, 2023, the entire contents of which are incorporated herein by reference.

TECHNICAL FIELD

The invention relates to a gas detection device (gas measuring device/gas detector) and a gas detection process (gas measuring process) which are capable of detecting a target gas and, depending on an instantaneous and/or an aggregated target gas concentration, optionally generating a respective warning or alarm (alert).

BACKGROUND

Such a gas detection device and such a gas detection process are used in particular to monitor a spatial area (spatial region) for at least one target gas that is harmful to a person. The spatial area is, for example, a production plant or the interior of a building or vehicle or aircraft. In particular, a user carries such a device with him/her while carrying out work in the spatial area. As a rule, the gas detection device generates an alarm in the event of a high target gas concentration and the user must leave the spatial area immediately.

SUMMARY

It is an object of the invention to provide a gas detection device and a gas detection process which in many cases make it easier for a user to work in a spatial area, in which area at least one target gas which is harmful to humans can occur, and in which the gas detection device and the gas detection process are capable of detecting this target gas.

The problem is solved by a gas detection device with features disclosed herein and by a gas detection process with features disclosed herein. Advantageous embodiments of the gas detection device according to the invention are, where appropriate, also advantageous embodiments of the gas detection process according to the invention and vice versa.

The gas detection device according to the invention and the gas detection process according to the invention are capable of detecting at least one target gas, optionally several target gases. The target gas or each target gas to be detected is in particular a toxic target gas, i.e. a gas which can be harmful to a human being if the human being is present in a spatial area which contains this target gas at a sufficiently high concentration. The or one target gas may also be a combustible gas.

The gas detection device according to the invention comprises a sensor unit. This sensor unit is configured to repeatedly measure an indicator of the current concentration of the target gas or of at least one target gas in a respective gas sample. "Respective" means that the sensor unit successively measures the concentration in different gas samples from the spatial area in order to measure the current target gas concentration. Of course the target gas concentration can vary over time. In one embodiment, the sensor unit is capable to measure the sum of the concentrations of several target gases in the gas sample. In another embodiment, the sensor unit is able to measure the respective concentration of several target gases.

The sensor unit is also able to generate a target gas signal and use measured values for the target gas concentration for this purpose. The generated target gas signal comprises a temporal sequence of target gas signal values. Each target gas signal value refers to one sampling time (sampling time point) of a given sequence of sampling times, in particular a sequence of equidistant sampling times. The signal value comprises the measured target gas concentration at this sampling time.

Optionally, the sensor unit can detect several target gases and generate a target gas signal for each target gas. Or the target gas signal describes the summed concentrations of several target gases at the sampling times.

The gas detection device according to the invention further comprises a signal-processing evaluation unit. This evaluation unit receives the target gas signal. The evaluation unit is capable to compare each target gas signal value with a specified smaller target gas threshold (lower target gas threshold) and a specified larger target gas threshold (upper target gas threshold). The smaller target gas threshold is a smaller threshold than the larger target gas concentration threshold. In particular, the two target gas thresholds are defined by or depend on legal and/or regulatory and/or internal company requirements.

If the target gas signal value is between the two target gas thresholds, the evaluation unit is capable to do the following: At least one target gas warning is issued (output) in a form that can be perceived by a human being. If the target gas signal value is greater than the larger target gas threshold, the evaluation unit is capable of the following: At least one target gas alarm is issued in a form that can be perceived by a human being. Optionally the warning and/or the alarm are issued in several forms that can be perceived by a human being.

Preferably, the larger target gas threshold is specified in such a way that a person suffers or may suffer damage to his/her health if the person is without suitable protective equipment in an area where the target gas concentration is above the larger target gas threshold. Immediate action is required in this situation, and thereby the alarm is issued. The warning or at least one warning is issued when the smaller target gas threshold is exceeded, but the larger target gas threshold is not yet exceeded. A person can use the warning as an indication to take at least one suitable corrective action so that the larger target gas threshold is not reached or a harmful effect on the user is avoided, for example to leave the spatial area or to ventilate it or to put on suitable protective equipment.

One possible embodiment has already been described above, namely that the sensor unit is able to generate a target gas signal for several predefined target gases. According to this embodiment, a smaller target gas threshold and a larger target gas threshold are preferably specified for each target gas that the sensor unit is able to detect. The thresholds may vary from target gas to target gas. The evaluation unit generates a warning for a target gas if a signal value for this target gas lies between the two target gas thresholds. It generates an alarm if the signal value is above the larger target gas threshold for this target gas.

The signal values of the target gas signal and the two target gas thresholds just described refer to a momentary situation, namely to the target gas concentration at a specific sampling time. However, a person can also be exposed to health risks if he/she is exposed to a relatively high target gas concentration over a longer period of time, even if this target gas concentration is never greater than the lower target gas threshold.

Therefore, the evaluation unit can also generate at least one aggregation signal. Just like the target gas signal, the aggregation signal or each aggregation signal comprises a temporal sequence of signal values, whereby each signal value of the aggregation signal relates to a respective reference time (reference time point). Each reference time is assigned to a respective sampling time and is equal to the sampling time or is positioned after the sampling time. Preferably, the sampling times of the target gas signal are also reference times of the aggregation signal. A reference time can also be after the assigned sampling time so that a calculation period between the sampling time and the reference time is available.

Each signal value of the aggregation signal or each aggregation signal comprises an aggregated value for the target gas concentration. The aggregated value is, in particular, an averaging or accumulation of target gas concentrations at the sampling times of an aggregation time period which time period comprises at least two, preferably at least ten, sampling times. As already explained, each signal value refers to a reference time. The aggregation time period ends at the reference time to which the signal value with the aggregated value refers. In other words: The reference time of the aggregation time period is assigned to the last sampling time of the aggregation time period.

An aggregated value is a signal value that is calculated by applying a specified calculation rule to several measured target gas concentrations at several different sampling times and thereby several target gas signal values. The sampling times lie within the aggregation time period. The calculation rule is configured as follows: if one target gas signal value increases and all other target gas signal values remain constant, the aggregated value also increases or at least remains constant. In other words: The calculation rule is monotonically increasing in each argument.

Important examples of the calculation rule that provides the aggregated value are a weighted mean or a median over a sliding time window, where the aggregation time period acts as the sliding time window and where the arithmetic mean is a special case of the weighted mean, an accumulation of all target gas signal values since a specified start and the maximum over all target gas signal values of the aggregation time period.

The weighted mean value and the median can become smaller again over time, namely when the target gas concentration decreases again. Accumulation, on the other hand, can only increase or remain constant.

In a first alternative, a time period is specified for the aggregation time period, whereby this time period is preferably at least 10 minutes, particularly preferably at least 15 minutes. The aggregation time period therefore moves with the advancing time (sliding time window). In a second alternative, the start of the aggregation time period is specified, for example as a time point. The time point can be predefined, for example by a user. Preferably, this specified time point is used as the time point at which the gas detection device use is initiated and the gas detection device is therefore switched on or at which a user has made a user input that he/she is now in a spatial area to be monitored and monitoring should begin. In the second alternative, the aggregation time period therefore becomes longer and longer and can cover the entire duration of the operation at the last scanning time of an operation. Preferably, the duration of the operation is at least 30 minutes, particularly preferably at least one hour, especially at least three hours.

In a first embodiment, the aggregated value is an average of the signal values of the target gas signal for the sampling times of the aggregation time period. Preferably, the duration of the aggregation time period is specified. In particular, the averaging can be the arithmetic mean, a weighted arithmetic mean or the median. For example, the younger (more recent) the signal values of the target gas signal (measured target gas concentrations), the higher the weighting factor. In the first embodiment, the aggregated value can remain the same, increase or decrease over time, depending on whether the target gas concentration remains the same, increases or decreases. Thus, in the first embodiment, the aggregated value is an indicator of an average exposure of a user in the aggregation time period.

In both embodiments of the aggregation signal, the aggregation time period has a duration of at least 5 minutes, preferably at least 10 minutes, particularly preferably at least 15 minutes. The aggregated value is therefore aggregated from target gas signal values that are distributed over a time span of at least 5 minutes. It is also possible for a single signal value of the target gas signal, i.e. a value for the current target gas concentration, to be generated from several individual measured values. However, the time span in which these measured values are measured and used to calculate the signal value has a duration of at most one minute, preferably at most half a minute.

In a second embodiment, the aggregated value is an accumulation of signal values for the sampling times of the aggregation time period, preferably of all signal values. An accumulation) of signal values is understood to be a weighted sum of the signal values over the aggregation time period. In particular, the weighting factors can all be the same or be greater the closer the sampling time is to the reference time. Preferably, the accumulation covers a time span of at least 5 minutes, particularly preferably at least 10 minutes, especially at least 15 minutes. Because an accumulation is performed, the aggregated value remains the same or increases, depending on whether the target gas is present or not, but does not decrease. If the target gas is present, the aggregated value increases. The aggregated value according to the second embodiment is a measure of the total, i.e. accumulated, exposure of the user since the start of the aggregation time period, for example since the start of an operation (a mission).

Not only a smaller target gas threshold and a larger target gas threshold are specified, but also a smaller aggregation threshold and a larger aggregation threshold are specified for each aggregation signal. Each aggregated value is a value of an aggregation signal for a reference time point. The evaluation unit is able to compare an aggregated value with both aggregation thresholds for the associated aggregation signal. If the aggregated value lies between the two aggregation thresholds, the evaluation unit triggers the following: At least one aggregation warning is issued in a form that can be perceived by a human being. If the aggregated value is greater than the larger aggregation threshold, the evaluation unit triggers the following: At least one aggregation alarm is issued in a form that can be perceived by a human being. In the case of several aggregation signals, the aggregation warning or an aggregation warning is issued if at least one aggregated value lies between the respective two aggregation thresholds, and the aggregation alarm or an aggregation alarm is issued if at least one aggregated value is greater than the respective larger aggregation threshold.

Both the target gas warning and the aggregation warning or each aggregation warning as well as the target gas alarm and the aggregation alarm or each aggregation alarm are issued in at least one of the following forms that a person can perceive with their senses: visually, acoustically and/or haptically (through vibrations).

A warning differs from an alarm in at least one way that can be perceived by a human being, for example by its volume (loudness) or brightness or frequency or amplitude, or by the fact that the warning is perceived as less intrusive than an alarm in another way. It is also possible that alarms and warnings are issued visually on different areas of an output unit. This difference applies both to a target gas alarm and a target gas warning and to an aggregation alarm and an aggregation warning.

According to the invention, the same gas detection device is thus capable of issuing at least four different messages in a form that can be perceived by a human being, namely at least two different alarms and at least two different warnings. These four messages can be distinguished from each other. Two possible messages relate to an instantaneous (current) value for the target gas concentration, while the other two possible messages relate to an aggregated value. The feature that the gas detection device is capable of issuing at least four differentiable (distinguishable) messages improves the monitoring of a spatial area and makes it easier for a user to take the correct action at an early stage to avoid a hazard. This effect is achieved in particular because, according to the invention, not only an alarm and a warning, but also at least one aggregation alarm and at least one aggregation warning can be issued.

The invention makes it easier to comply with legal and/or regulatory and/or internal company requirements. Such requirements often require that an alarm is issued both when an instantaneous target gas concentration is above a threshold and when a target gas concentration aggregated over an aggregation time period is above a threshold. In accordance with the invention, an upper target gas threshold and at least one upper aggregation threshold are used.

As a rule, safety regulations require that a user must leave a certain spatial area immediately if an alarm is issued, whether due to an instantaneous or an aggregated target gas concentration. The user must leave a work in progress. In many cases, the invention means that a user receives an announcement, namely a warning, and can take appropriate countermeasures before the instantaneous or aggregated target gas concentration has become so high that the user must immediately leave the area being monitored. In particular for this reason, the invention makes it easier in many cases to stay in a monitored spatial area and carry out work there compared to a conventional gas detection device. Thanks to the invention, it is often less necessary for a user to suddenly interrupt or abandon work that has been started. Possible countermeasures that a user can take after a warning has been issued in accordance with the invention are as follows:

The user now wears suitable protective equipment, preferably including at least one filter for ambient air, so that the user can inhale filtered ambient air that is ideally free of the harmful target gas or any harmful target gas.

The user ensures greater ventilation of the area to be monitored.

The user closes a possible source of a harmful target gas, for example a leak in a container or pipe.

The user completes a current task and then leaves the area to be monitored in which a detected target gas occurs.

Thanks to the warning, the user does not need to leave the area to be monitored immediately and does not need to interrupt any work that has started.

In the application just described, a high target gas concentration is dangerous for a human being. A gas detection device according to the invention can also be used to detect a low target gas concentration, in particular a low oxygen concentration. In this alternative application, the features "greater than the larger target gas threshold" and "greater than the larger aggregation threshold" are to be replaced by "less than the smaller target gas threshold" and "less than the smaller aggregation threshold" respectively.

In many cases, the invention can be implemented relatively easily on an existing gas detection device. It is often sufficient to install new software on a control unit or on a separate evaluation unit of an existing gas detection device. As a rule, the invention does not require existing hardware to be modified. This is due in particular to the fact that the invention can be used in combination with many conventional principles to detect a target gas and/or to measure its concentration.

In many cases, the invention can also be implemented on an existing gas detection device if this existing gas detection device already has regulatory or internal company approval. The regulatory approval is retained even if the invention is implemented. This is because a regulatory approval generally relates to threshold values, the exceeding of which must lead to the issue of an alarm, and optionally to the reliability of a gas detection device. In many cases, however, these required properties are not changed by the invention. Rather, the invention complements a function to the gas detection device.

Preferably, the sensor unit comprises a target gas sensor and a detection variable sensor. The target gas sensor has a detection variable that correlates with the concentration of the target gas or at least one target gas to be detected, usually an electrical detection variable. The target gas sensor comprises a photodetector, for example, and the detection variable correlates with the intensity of incident electromagnetic radiation. Or the target gas sensor causes a chemical reaction that correlates with the concentration of the target gas. Or the target gas sensor is able to oxidize combustible target gas. The detection variable sensor is able to repeatedly measure an indicator of the detection variable, i.e. to measure what value the detection variable is currently assuming. If combustible target gas is oxidized, the detection variable sensor is able to measure an indicator of the thermal energy which is released when oxidizing the target gas. To generate the target gas signal, the sensor unit uses measured values from the detection variable sensor and applies a predefined functional relationship to the measured values. This relationship describes the relationship between the target gas concentration and the detection variable and is preferably determined in advance, preferably empirically. The relationship can be specific to the gas detection device.

In one embodiment, the evaluation unit is able to calculate two aggregation signals, namely a first aggregation signal according to the first embodiment and a second aggregation signal according to the second embodiment. The gas detection device is thus able to issue a total of six different messages. For the first aggregation signal, a sliding (rolling, moving) aggregation time period of fixed duration is specified, preferably of at least 10 minutes duration, for the second aggregation signal an aggregation time period with a fixed starting time (beginning). The second aggregation time period therefore becomes longer and longer. According to this embodiment, two smaller aggregation thresholds and two larger aggregation thresholds are specified, namely a smaller and a larger aggregation threshold for the first aggregation signal and a smaller and a larger aggregation threshold for the second aggregation signal. The two smaller aggregation thresholds can be the same or different from each other. The two larger aggregation thresholds can also be the same or different from each other.

The configuration in which the evaluation unit calculates two aggregation signals has the following effect: The gas detection device is capable of detecting both a high averaged target gas concentration in a sliding time window and a high cumulative target gas concentration since a defined starting time, independently of each other. Either of these two situations can lead to a health hazard. A user receives a warning if at least one of the two larger aggregation thresholds is about to be exceeded and an alarm if the aggregated value of at least one of the two larger aggregation thresholds is exceeded.

According to the invention, a smaller target gas threshold, a larger target gas threshold and, for the or each aggregation signal, a smaller aggregation threshold and a larger aggregation threshold are specified. In one embodiment, the smaller aggregation threshold or each smaller aggregation threshold is equal to the smaller target gas threshold, and the larger aggregation threshold or each larger aggregation threshold is equal to the larger target gas threshold.

In a preferred embodiment, however, the smaller aggregation threshold or at least one smaller aggregation threshold is smaller than the smaller target gas threshold. Alternatively, or additionally, in a preferred embodiment, the larger aggregation threshold or at least one larger aggregation threshold is smaller than the larger target gas threshold. It is even possible that the smaller target gas threshold is larger than (greater than) the larger aggregation threshold or at least one or even every larger aggregation threshold.

This embodiment is particularly useful if a compromise is to be found between the following two requirements:

On the one hand, a user should also be warned or alerted if a target gas concentration has occurred that is only relatively slightly above a design-related detection limit of the gas detection device. According to the embodiment, this is achieved by the fact that a smaller aggregation threshold, optionally even a larger aggregation threshold, is relatively small and preferably less than twice the detection limit.

On the other hand, relatively few false alarms and false warnings should occur. Therefore, the smaller target gas threshold should be sufficiently large.

The embodiment just described enables the following: The two target gas thresholds are set so high that the risk of a false alarm, in this case a false target gas alarm, and the risk of a false warning due to an incorrect measurement of the target gas concentration are relatively low. In contrast, the two aggregation thresholds—or at least one aggregation threshold—are set so low that a warning and then an alarm are generated and issued relatively reliably even if the target gas concentration is only slightly above the detection limit for a longer time period but which concentration is nevertheless to be detected. If the evaluation unit is able to calculate two aggregation signals, at least the two aggregation thresholds (smaller threshold and larger threshold) for an aggregated value obtained by averaging are preferably set lower than the two corresponding target gas thresholds.

According to the invention, the evaluation unit of the gas detection device is capable of causing at least one warning or at least one alarm to be issued in a form that can be perceived by a human being, depending on the instantaneous and the aggregated target gas concentration. In one embodiment, the gas detection device comprises a communication unit via which a data connection can at least temporarily be established between the gas detection device and a spatially remote receiver. The gas detection device is capable of causing a message comprising either a warning or an alarm to be transmitted from the communication unit to the receiver via the data connection. The receiver issues a message with the warning or alarm in a form that can be perceived by a human being. This embodiment eliminates the need to provide the gas detection device itself with an output unit. It can be used in particular for a stationary gas detection device. A user of the receiver can trigger an appropriate action when the receiver emits a warning or an alarm.

In another embodiment, the gas detection device additionally comprises at least one output unit, which is preferably embedded in a housing of the gas detection device. For example, the gas detection device is a portable device carried by a person while the person is in a spatial area in which at least one target gas to be detected may occur. This portable device preferably also comprises a power supply unit. The evaluation unit or a control unit of the gas detection device is able to control this output unit. In response to a corresponding activation, the output unit issues a warning or an alarm in at least one form that can be perceived by a human being. This configuration eliminates the need for data communication with a remote receiver, but can also be used in combination with a remote receiver.

In one embodiment, the gas detection device comprises a visual output unit and at least one further output unit. The visual output unit can selectively issue a warning or an alarm in a form that can be visually perceived by a human being. Preferably, the visual output unit issues on the one hand a visually perceptible symbol, whereby the symbol for a warning differs from the symbol for an alarm, and on the other hand a numerical value for an instantaneous or aggregated target gas concentration, for example in ppm (parts per million). It is possible that the numerical value is displayed larger and/or in a different color when an alarm is issued than when a warning is issued.

The further output unit or each further output unit can optionally issue a warning or an alarm in a way that can be perceived acoustically and/or haptically by a human being, in particular as a vibration. The acoustic and/or haptic output for a warning differs from the corresponding output for an alarm, for example by a different brightness or volume or frequency or amplitude or by the fact that the output for a warning is in a different way less intrusive (pushy) than the output for an alarm. For example, the output by the further output unit includes the step of emitting a pulsed sound, whereby the pulse frequency or pulse duration or pulse amplitude is greater for an alarm than for a warning. Accordingly, in the case of a haptic output, the frequency or amplitude of the vibration can be greater in the case of an alarm than in the case of a warning.

In one embodiment, the further output unit or a further output unit is capable of issuing a first message for a warning and a second message for an alarm, the two messages being different from one another and both being perceptible by a human being acoustically and/or haptically, but not necessarily visually. The controlled evaluation unit or a control unit controls the further output unit as follows: The further output unit issues the first message, i.e. the message for a warning, if a target gas signal value is between the two target gas thresholds or if an aggregated value is between the two aggregation thresholds. A message about these two events is therefore issued acoustically and/or haptically in the same way. The controlled further output unit issues the second message, i.e. the message for an alarm, if a target gas signal value is larger than the larger target gas threshold or if an aggregated value is greater than the greater aggregation threshold. The message for the alarm is also issued in the same way, i.e. when the larger target gas threshold is exceeded in the same way as when the larger aggregation threshold or a larger aggregation threshold is exceeded.

This embodiment takes into account in a particularly ergonomic way the fact that a user perceives an acoustic and a haptic message even if the user is busy with something else and is not looking at the gas detection device. Therefore, in many cases an exclusively visual output is not sufficient. On the other hand, a user is generally only able to reliably distinguish between a few acoustic and only a few haptic messages, especially if other acoustic and/or haptic impressions (sensory inputs), in particular ambient noise, are present. Therefore, in some cases it is not sufficient if a user is only informed acoustically and/or only haptically, but not visually. In many cases, an output by the further output unit, or one further output unit, will cause the user to look at the visual output unit and get more detailed information about the warning or alarm—or to realize that the acoustic or haptic impression (sensory input) comes from another source and is neither a warning nor an alarm.

In one embodiment, the gas detection device comprises an actuating element, in particular a physical button or a touchscreen. A user of the gas detection device can actuate this actuating element. Actuation of the actuating element causes the output of a warning to be terminated. On the other hand, the output of an alarm continues even if the actuating element has been actuated. This configuration is particularly ergonomic for the following reason: If a user receives a warning, he/she can in many cases take a measure to prevent the target gas concentration from reaching a higher threshold or at least continue work that has been started. By pressing the actuating element, the user confirms that he/she has noticed the warning. A further output of the warning would be perceived as useless and annoying. On the other hand, the user usually has to leave the area immediately when an alarm is issued. It is therefore not usually desirable for a user to be able to "push away" an alarm, i.e. switch it off and then forget about it.

According to the invention, a smaller target gas threshold, a larger target gas threshold, at least one smaller aggregation threshold, and at least one larger aggregation threshold are specified. In one embodiment, a user specifies all at least four thresholds. In another embodiment, one factor is specified. This factor is greater than 0 and less than 1 and preferably greater than or equal to 0.5. A user specifies the larger target gas threshold and the larger aggregation threshold or each larger aggregation threshold, and optionally also the factor. The evaluation unit automatically derives the smaller target gas threshold as the product of the factor and the upper target gas threshold. In addition, the evaluation unit derives the smaller aggregation threshold as the product of the factor and the upper aggregation threshold. Optionally, the evaluation unit derives each lower aggregation threshold as a product of the factor and the corresponding upper aggregation threshold. This embodiment with the factor saves a user from having to specify all at least four thresholds.

The gas detection device according to the invention is capable of issuing at least four different messages, in one embodiment even six different messages. In two embodiments described below, the number of possible messages can be reduced. This is achieved by allowing the gas detection device to selectively be operated in one of at least two different possible modes. For example, a user selects a mode using a selection unit. Or the mode in which the gas detection device is to be operated is defined in advance and stored in a data memory. In both implementations, it is possible for the same gas detection device to be operated in at least two different modes in succession.

The embodiment with the different modes increases the flexibility with which the gas detection device can be used. In a mode in which the number of possible messages is reduced, in some cases a user is prevented from being overstimulated. The mode in which the gas detection device is to be operated may depend on a target gas for which a spatial area is to be monitored using the gas detection device. In many cases, this embodiment avoids the need to provide different gas detection devices for different applications. Rather, the same gas detection device or at least several identical gas detection devices can be used for different applications, with only different modes being set.

Various implementations are described below, showing how the design can be realized with the different modes. Several realization forms can also be combined with each other, i.e. realized simultaneously.

In one implementation, the gas detection device can optionally issue both alarms and warnings (one possible mode) or only alarms (another possible mode).

In one implementation, the gas detection device can optionally issue alarms and warnings on the basis of both an instantaneous signal value and an aggregated signal value (one possible mode) or only on the basis of an instantaneous signal value (another possible mode).

In one implementation, the evaluation unit is able to generate a first aggregation signal and a second aggregation signal, for example as an accumulation since a certain time point or as a weighted average value over a sliding time window. In one possible mode, the gas detection device is able to issue six different possible messages, namely an alarm and a warning based on an instantaneous value, and two alarms and two respective warnings based on every aggregation signal each. In two other possible modes, the gas detection device is only able to issue four different possible messages, namely also an alarm and a warning based on an instantaneous value, and an alarm and a warning based on the first and second aggregation signals respectively, but not on the second and first aggregation signals respectively. A fourth mode is also possible, in which the gas detection device is only able to issue two different possible messages, namely an alarm and a warning based on an instantaneous value.

According to the invention, the evaluation unit compares instantaneous target gas signal values and aggregated values with predefined thresholds. In one embodiment, the gas detection device comprises its own input unit for capturing thresholds.

In another implementation, the gas detection device is at least temporarily in a wired or wireless data connection with a remote input unit. A user can use this remote input unit to specify and enter values for the thresholds of the gas detection device. These values are transmitted from the input unit to the gas detection device and stored in a data memory of the gas detection device. The embodiment with the spatially remote input unit makes it easier for a user to specify in one step thresholds for a set of gas detection devices according to the invention. A step is triggered that includes transmitting the entered values from the input unit to each device of the set of gas detection devices.

These two implementations can be combined with each other. For example, a technician specifies thresholds for a set of gas detection devices according to the invention in advance using the remote input unit. A user of a particular gas detection device of the set can change a threshold for that gas detection device.

The invention is described below by means of embodiment examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
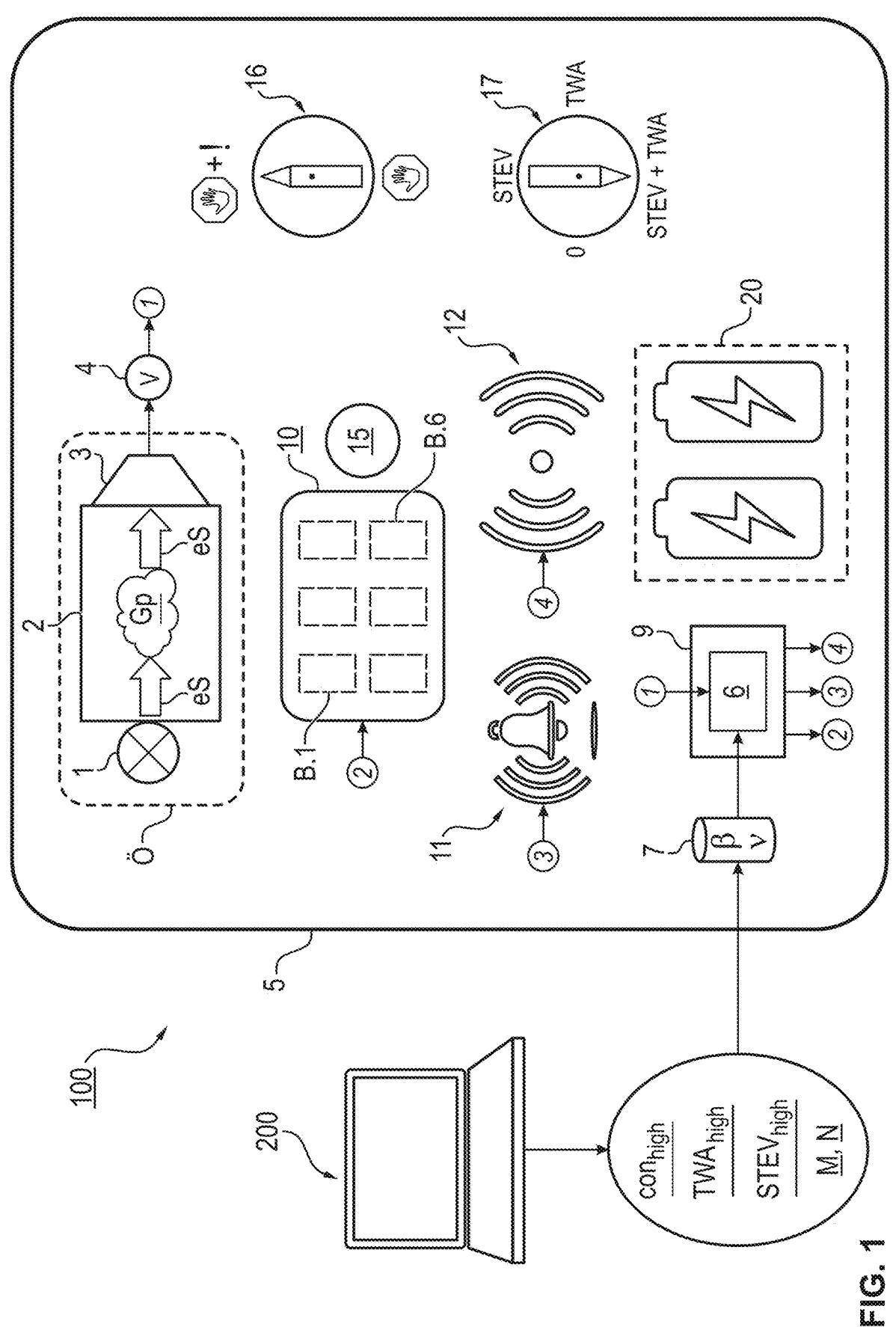
FIG. 1 is a schematic view of a structure and configuration of the gas detection device according to the invention.

Referring to the drawings, in an embodiment example, the gas detection device according to the invention is configured as a portable device. A user carries this portable device while the user is in a spatial area in which at least one target gas that is harmful to a human being may occur. In particular, this target gas can impede a person's breathing, for example by attacking the respiratory tract and/or the blood circulation and/or the nervous system, or can be carcinogenic. The portable device is attached to the user's protective clothing, for example.

It is also possible to use the gas detection device according to the invention in an operating theater. The patient is or will be anaesthetized with the aid of a ventilation circuit. In the ventilation circuit, the patient is supplied with a mixture of respiratory gas and at least one anesthetic agent. The target gas or a target gas is in this case the anesthetic agent or an anesthetic agent, which can escape into the operating theatre in an undesirable manner and anaesthetize people who want to treat a patient.

The user prefers to use the gas detection device during a shift that lasts between five and eight hours, for example. During this shift, the user may be exposed to harmful target gases. It is possible that the shift is interrupted because the user is in an environment that is free of harmful target gases, for example because the user is traveling from one work location in a vehicle to another work location or is taking a break from work.

A higher (upper) target gas threshold is specified by legal or regulatory or even internal company regulations, for example with the measuring unit ppm. As soon as the concentration of the target gas or a target gas or the total concentration of several target gases reaches or exceeds this higher target gas threshold, the user must leave the monitored area immediately. In the embodiment example, it is also specified that the user must also leave the area immediately if a target gas concentration aggregated over a period of time exceeds an aggregation threshold. This aggregation is described in more detail below. In both situations, the gas detection device generates and issues an alarm, which is also described below.

The gas detection device comprises a housing. A measuring chamber, a sensor unit, a signal-processing evaluation unit, a signal-processing control unit and a separate power supply unit are arranged inside the housing. The evaluation unit can be a component of the control unit. It is possible that the evaluation unit is implemented as a software program that is stored in a data memory of the control unit and runs on a processor of the control unit when the gas detection device is used.

The sensor unit comprises a target gas sensor and a detection variable sensor. The target gas sensor is preferably arranged in or on the measuring chamber and is influenced by a target gas to be detected. The target gas sensor has a detection variable which correlates with the concentration of the target gas or at least one target gas and which is measurable. In many cases, this detection variable is an electrical variable, for example the electrical voltage or the electrical current or the electrical charge or even the electrical resistance.

The measuring chamber is at least temporarily in a fluid connection with the environment and thus with a spatial area to be monitored. Preferably, this fluid connection is interrupted when the gas detection device is not in use. A gas sample can flow from the area into the measuring chamber, for example by being sucked in and/or by diffusing into the measuring chamber on its own. The detection variable sensor repeatedly measures an indicator of the detection variable. Preferably, the measuring chamber is regularly purged so that the gas sample in the measuring chamber corresponds sufficiently accurately with the gas in the spatial area to be monitored.

FIG. 1 schematically and exemplarily shows a gas detection device 100 with a sensor unit and a housing 5. The exemplarily described sensor unit comprises a radiation source 1, a measuring chamber 2, a photoelectric detector 3 and a voltage sensor 4. A gas sample Gp, shown schematically, is located in the measuring chamber 2. This gas sample Gp originates from a spatial area to be monitored and has entered the measuring chamber 2 through the opening Ö in the housing 5. Preferably, the measuring chamber 2 is repeatedly purged (flushed out) of an old gas sample so that a new gas sample can enter the measuring chamber 2.

The radiation source 1 emits electromagnetic radiation eS into the measuring chamber 2. At least some of the electromagnetic radiation eS penetrates the gas sample Gp at least once and then strikes the detector 3. A target gas in the measuring chamber 2 attenuates the intensity of the electromagnetic radiation eS in a wavelength range that depends on the target gas, compared to a state without target gas. An electrical voltage is present at the output of the detector 3. The voltage sensor 4 shown as an example measures the voltage at the output of the detector 3 and generates measured values. The voltage and thus the measured values correlate with the intensity of the incident electromagnetic radiation eS. The detector 3 therefore acts as the target gas sensor, the voltage sensor 4 as the detection variable sensor.

The sensor unit can, for example, also be configured as an electrochemical sensor that functions in the manner of a fuel cell. The electrical charge that flows between a measuring electrode and a counter electrode is the preferred detection variable.

A functional relationship is specified, for example a proportional factor B. This functional relationship describes the relationship between the target gas concentration and the detection variable. As a rule, the larger the target gas concentration, the larger or smaller the detection variable.

FIG. 1 also schematically shows a signal-processing evaluation unit 6, which is part of a control unit 9. At least temporarily, the evaluation unit 6 has read access to a data memory 7, in which the predefined functional relationship $\beta$ is stored in computer-evaluable form. In addition, a power supply unit 20 is shown schematically, which supplies the electrical loads of the gas detection device 100 with electrical energy independently of a stationary power supply network.

The evaluation unit 6 applies the specified functional relationship $\beta$ to the measured values of the detection variable sensor 4 and thereby generates a target gas signal. This target gas signal comprises a temporal sequence of target gas signal values. Each target gas signal value relates to a respective sampling time and comprises information about the target gas concentration at this sampling time. This target gas concentration was derived by applying the functional relationship $\beta$ to at least one measured value that relates to this sampling time. Optionally, signal pre-processing is carried out in advance for several measured values in order to generate a signal value for a sampling time. The signal pre-processing can in particular include smoothing.

In the embodiment example, the sampling times t(0), t(1), t(2), . . . are preferably equidistant, i.e. have the form t(i)=t0+i*Δt with a specified sampling rate f=1/Δt. Use of the gas detection device 100 begins at the time t(0)=t0. This time is, for example, the start of a shift. The operation ends, for example, at the end of the shift. The target gas signal value, i.e. the target gas concentration, at time t(i) is denoted by con(i) (i=0, 1, 2, . . . ).

The evaluation unit 6 receives and processes the target gas signal. A smaller target gas threshold $con_{low}$ and a larger target gas threshold $con_{high}$ are stored in the data memory 7 or in a program that the evaluation unit 6 executes in a form that can be evaluated by a computer.

In a preferred embodiment, the gas detection device 100 is temporarily in a data connection with a remote input unit 200 before use. A technician uses this input unit 200 to specify the larger thresholds used by the evaluation unit 6 and thus also the larger target gas threshold $con_{high}$. Each smaller threshold is equal to the product of a specified and stored factor Y and the corresponding upper threshold that the technician has specified using the input unit 200. For example, the factor $\gamma$ is 50% or 70% or 75%. As a rule, these thresholds are used for several uses of the same gas detection device 100.

The smaller target gas threshold $con_{low}$ is therefore, for example, equal to half or three quarters of the larger target gas threshold $con_{high}$. In one application, the larger target gas threshold $con_{high}$ is 10 ppm and the smaller target gas threshold $con_{low}$ is 5 ppm. It is also possible to specify different factors.

The evaluation unit 6 checks on the one hand whether a warning event has occurred and on the other hand whether an alarm event has occurred. In the embodiment example, the warning event has occurred if the target gas signal value, which relates to the most recent sampling time, is greater than or equal to the smaller target gas threshold $con_{low}$ and smaller than the larger target gas threshold $con_{high}$. The alarm event has occurred if this target gas signal value is greater than or equal to the upper target gas threshold $con_{high}$. If the warning event has occurred, the evaluation unit 6 generates a target gas warning. If the alarm event has occurred, the evaluation unit 6 generates a target gas alarm.

Figure 2:
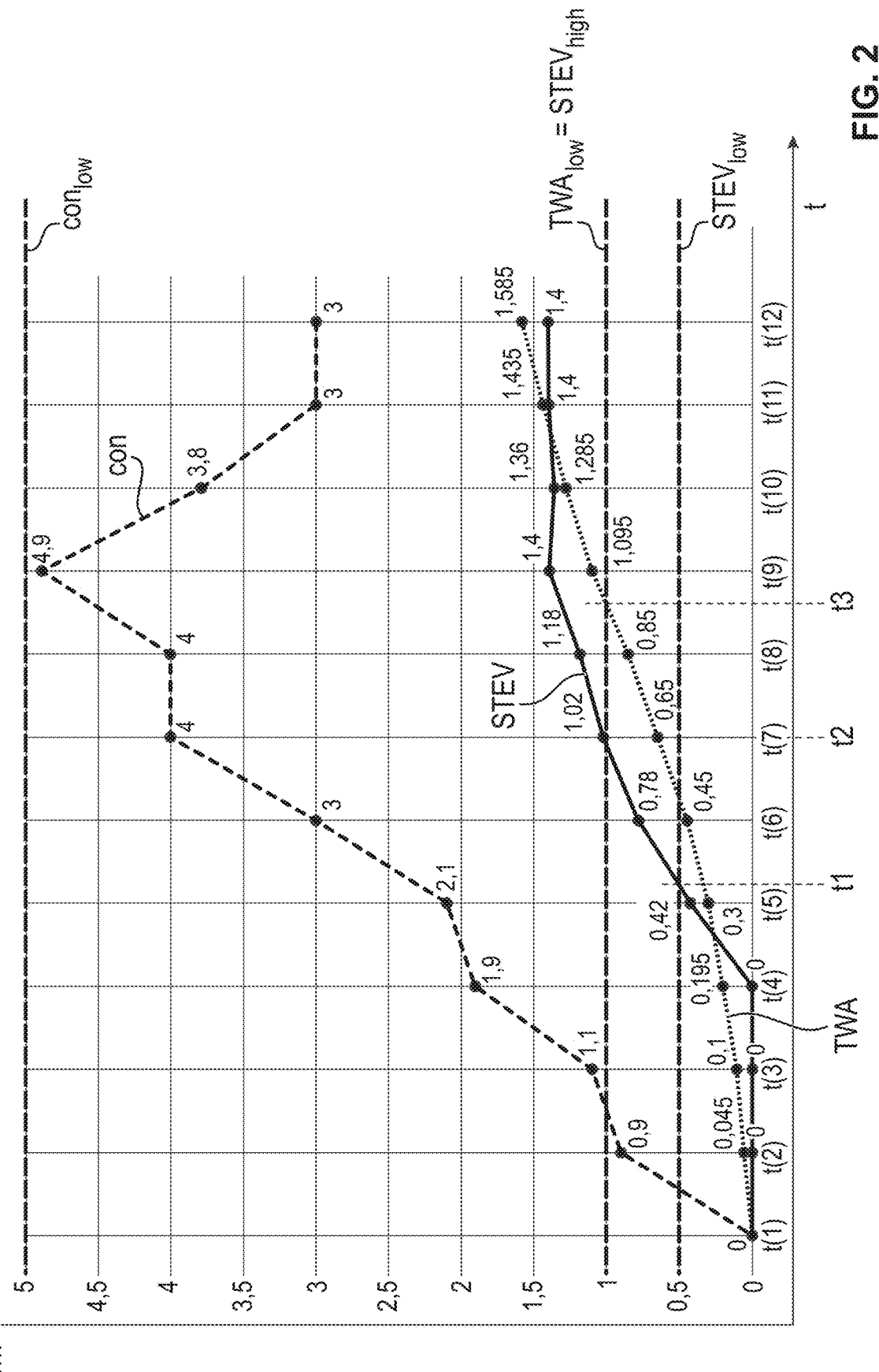
FIG. 2 is a graph showing three exemplary time courses, namely con, STEV and TWA.

FIG. 2 shows an example of three time courses. The time is plotted on the x-axis and the target gas concentration in [ppm] on the y-axis. The time course marked with con shows the respective target gas signal value at twelve sampling times t(1) to t(12). The smaller target gas threshold $con_{low}$=5 ppm is also shown. The two remaining time courses are explained below. In the example shown, the target gas concentration con does not reach the smaller target gas threshold $con_{low}$.

The gas detection device 100 of the embodiment example comprises a visual output unit and at least one further output unit. The control unit 9 is able to control all output units, depending on a signal from the evaluation unit 6.

FIG. 1 schematically shows a visual output unit 10 with a screen, an acoustic output unit 11 and a haptic output unit 12. The three output units 10, 11, 12 are explained below.

Figure 3:
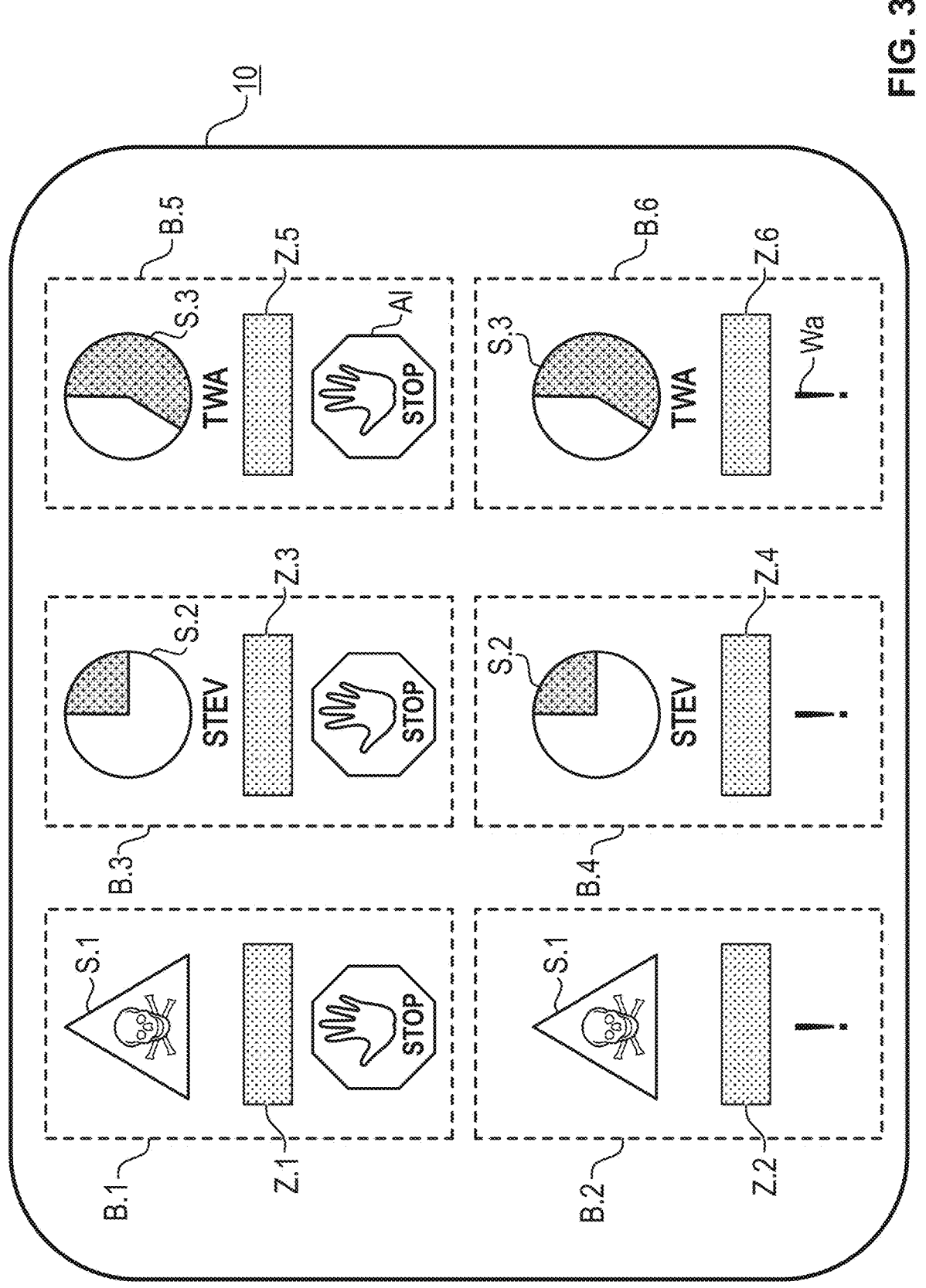
FIG. 3 is a schematic view showing an example of a screen with six screen areas.

The visual output unit 10 is able to issue messages in a form that a person can perceive visually. In particular, a message can be triggered by a warning event or an alarm event. In the embodiment example, the visual output unit 10 comprises a screen which is embedded in the housing of the gas detection device 100 and comprises six non-overlapping screen areas B.1 to B.6. FIG. 3 shows an example of such a screen 10 and the six screen areas B.1 to B.6.

A symbol is displayed in each screen area B.1 to B.6, and the screen area B.1 to B.6 also includes an output area Z.1 to Z.6 for a numerical output. A first screen area B.1 is assigned to the target gas alarm, a second screen area B.2 to the target gas warning. The two screen areas B.1 and B.2 each include a symbol S.1 for a toxic target gas. It is possible that the gas detection device 100 is capable of detecting at least two different toxic target gases and is therefore capable of displaying different symbols in areas B.1 and B.2. The screen areas B.1, B.3 and B.5 also include a symbol Al for an alarm. The screen areas B.2, B.4 and B.6 also include a symbol Wa for a warning. The symbols and the arrangement of screen areas B.1 to B.6 are to be understood as examples only.

If the evaluation unit 6 has generated a target gas warning, the target gas symbol S.1 and the warning symbol Wa are highlighted in the second screen area B.2, whereby in one implementation the target gas symbol S.1 indicates the detected target gas. In addition, the target gas concentration that led to the warning event is displayed numerically in the output area Z.2 of the second screen area B.2. If the evaluation unit 6 has generated a target gas alarm, the target gas symbol S.1 and the alarm symbol Al are highlighted accordingly in the first screen area B.1, and the target gas concentration that led to the alarm event is displayed numerically in the output area Z.1 of the first screen area B.1. Optionally, the target gas to which the warning or alarm and the numerical value relate is also displayed.

In the embodiment example, the further output unit 11 is capable of emitting both a warning and an alarm acoustically, and the further output unit 12 haptically. The further output unit 11 emits a warning and an alarm acoustically by emitting a pulsed sound or a sound with a sinusoidal characteristic, i.e. swelling and decaying (rising and falling). The volume and/or the pulse frequency or pulse duration and/or the pulse amplitude is greater for an alarm than for a warning, so that the output of an alarm can be distinguished acoustically from the output of a warning. The further output unit 12 emits a warning and an alarm haptically, namely by vibrations. The frequency and/or amplitude of the vibration is greater for the haptic output of an alarm than for the haptic output of a warning. This means that the haptic output of an alarm can also be distinguished from the output of a warning.

The feature that the gas detection device 100 with the two further output units 11 and 12 emits a warning and an alarm both visually and acoustically as well as haptically increases reliability, especially if the gas detection device 100 is used in a noisy environment, so that an acoustic output could be overheard, and/or if the gas detection device 100 is attached to protective clothing, so that a vibration could not be perceived.

In the embodiment example, the evaluation unit 6 generates a first aggregation signal and a second aggregation signal and uses the target gas signal for a generation of these. Both aggregation signals comprise a temporal sequence of aggregation signal values, with each aggregation signal value relating to a reference time. In one implementation, these reference times are the sampling times t(1), t(2), . . . of the target gas signal. In another implementation, each reference time is a specified fixed time period following a sampling time, whereby this time period is used, for example, for the calculations required for aggregation. The unit of measurement of the two aggregation signals is that of the target gas concentration, i.e. also ppm, for example.

A time duration is provided for the first aggregation signal, for example 15 minutes. The first aggregation signal is an averaging of the target gas signal values over a sliding time window, whereby the duration of this time window is equal to the specified time duration and whereby this time window ends at the most recent sampling time t(n). The first aggregation signal thus describes the average load of the user in this sliding time window. The first aggregation signal is referred to as STEV (short-time exposure value) and indicates the average exposure of the user in the sliding time window. The signal value of the first aggregation signal STEV at the reference time t'(n) for the sampling time t(n) is referred to as STEV(n). The sliding time window at time t(n) covers the N most recent sampling times t(n−N+1), . . . , t(n), where N*Δt is the specified duration of 15 minutes, for example. The evaluation unit 6 applies the formula $$STEV(n) = \frac{\sum_{i=1}^{N} con(n - N + i)}{N}. \tag{1}$$

In one embodiment, weight factors α(1), . . . , α(n) are specified with $$\sum_{i=1}^{N} \alpha(i) = 1$$

and with α(1)<=α(2)<= . . . <=α(N). The evaluation unit 6 applies the calculation rule $$STEV(n) = \frac{\sum_{i=1}^{N} \alpha(i) * con(n - N + i)}{N}. \tag{2}$$

The more recent target gas concentrations are then rated higher than the older ones. It is also possible that the evaluation unit 6 calculates the aggregated value STEV(n) as the median of the N signal values con (n−N+1), . . . , con (n).

The second aggregation signal describes the user's previous accumulated exposure during use and is referred to as TWA (time-weighted average). TWA(n) is the aggregated value at the reference time t'(n). For the second aggregation signal TWA, a time point is provided as the start. In the embodiment example, this is the first sampling time, i.e. the time t(0) at which the use of the gas detection device 100 begins. During use, for example in the course of the shift of e.g. 8 hours duration, the current target gas concentration is measured at a total of M sampling times. The shift therefore has a total duration of M*Δt. The evaluation unit 6 preferably applies the following calculation rule:

$$TWA(n) = \frac{\sum_{i=1}^{n} con(i)}{M}. \tag{3}$$

Obviously, TWA(1)<=TWA(2)<= . . . <=TWA(M). It is again possible to specify weighting factors α(1)<= α(2)<= . . . <=α(n), so that the most recent concentration values are rated higher than older ones.

FIG. 2 shows an example of a section of the two time histories for the two signals STEV and TWA. The number M of sampling points in an operating period is 20, the number N for the sliding time window is 5. As a rule, N<=M.

At time t1, the first aggregation signal STEV exceeds the smaller first aggregation threshold $STEV_{low}$, and a warning is issued in screen area B.4. At time t2, the first aggregation signal STEV exceeds the larger first aggregation threshold $STEV_{high}$, and an alarm is issued in screen area B.3. A user of the gas detection device 100 must now leave the monitored spatial area immediately. At time t3, the second aggregation signal TWA exceeds the smaller second aggregation threshold $TWA_{low}$, and a warning is issued in screen area B.6.

With the aid of the input unit 200 described above, a technician specifies a first larger aggregation threshold $STEV_{high}$, i.e. a larger aggregation threshold for the first aggregation signal STEV, and a second larger aggregation threshold, i.e. a larger aggregation threshold $TWA_{high}$ for the second aggregation signal TWA, see FIG. 1. In one application, the first larger aggregation threshold $STEV_{high}$ is 1 ppm, and the second larger aggregation threshold $TWA_{high}$ is 2 ppm. The evaluation unit 6 derives a smaller aggregation threshold $STEV_{low}$ for the first aggregation signal STEV and a smaller aggregation threshold $TWA_{low}$ for the second aggregation signal TWA, for example as half of the respective larger threshold $STEV_{high}$, $TWA_{high}$. In the application just mentioned, the first smaller aggregation threshold $STEV_{low}$ is therefore 0.5 ppm, and the second smaller aggregation threshold $TWA_{low}$ is 1 ppm. The technician also preferably enters the values M and N.

In the embodiment example, the aggregation thresholds are therefore smaller than the target gas thresholds. The first smaller aggregation threshold $STEV_{low}$ is not very much above the detection limit of the sensor unit 1 to 4, for example it is at most twice as large as the detection limit. Because the first smaller aggregation threshold $STEV_{low}$ is smaller than the smaller target gas threshold $con_{low}$, in one application ten times smaller, on the one hand a user is warned even at a relatively low target gas concentration. Because this warning results from exceeding the first smaller aggregation threshold $STEV_{low}$, i.e. from averaging over a sliding time window, the risk of a warning being generated by mistake is relatively low. The smaller target gas threshold $con_{low}$ is significantly larger, so that the risk of a single incorrect measured value falsely leading to a warning is low.

The evaluation unit 6 causes both the visual output unit 10 and the other output units 11, 12 to each issue a warning if at least one of the following two events has occurred:

The current signal value of the first aggregation signal STEV is above the first smaller aggregation threshold $STEV_{low}$.

The current signal value of the second aggregation signal TWA is above the second smaller aggregation threshold $TWA_{low}$.

Accordingly, the evaluation unit 6 causes both the visual output unit 10 and the other output units 11, 12 to each issue an alarm if at least one of the following two events has occurred:

The current signal value of the first aggregation signal STEV is equal to or above the first larger aggregation threshold $STEV_{high}$.

The current signal value of the second aggregation signal TWA is equal to or above the second larger aggregation threshold $TWA_{high}$.

As already explained above, thanks to the further output units 11 and 12, the gas detection device 100 is able to issue a warning and an alarm in both an audible and a haptically perceptible manner. The warning when the smaller target gas threshold $con_{low}$ is exceeded or when a smaller aggregation threshold $STEV_{low}$, $TWA_{low}$ is exceeded is issued in the same way each time, and the respective alarm is also issued in the same way each time. The other output units 11, 12 can therefore only issue a total of two different types of messages. A user can distinguish between these two types relatively easily acoustically and haptically.

The first screen area B.1 and the second screen area B.2 are assigned to the two target gas thresholds $con_{high}$, $con_{low}$, the third screen area B.3 and the fourth screen area B.4 are assigned to the two first aggregation thresholds $STEV_{high}$, $STEV_{low}$ and the fifth screen area B.5 and the sixth screen area B.6 are assigned to the two second aggregation thresholds $TWA_{high}$, $TWA_{low}$. The first, third and fifth screen areas B.1, B.3, B.5 are used to issue an alarm, the second, fourth and sixth screen areas B.2, B.4, B.6 are used to issue a warning. The third, fourth, fifth and sixth screen areas B.3 to B.6 also each comprise an aggregation symbol, namely the symbol S.2 for STEV or the symbol S.3 for TWA as well as the alarm symbol Al or the warning symbol Wa. In addition, they each include an output area Z.3, ..., Z.6 to numerically output a target gas concentration. If the output unit 10 performs the operation of issuing a warning or alarm related to an aggregation threshold, the corresponding symbol S.2, S.3 is highlighted. In addition, the aggregated value that led to the warning or alarm is displayed in the corresponding output area Z.3, ..., Z.6. Optionally, the type of target gas is also displayed.

Preferably, an actuating element 15 is also embedded in the housing 5, e.g. to the right of the visual output unit 10, see FIG. 1. By actuating the actuating element 15, the user confirms that he/she has taken note of a warning or an alarm. If this confirmation relates to a warning, the control unit 9 preferably causes the warning output to be terminated. On the other hand, the output of an alarm is continued even if the user has actuated the actuating element 15. If an alarm is issued and the user has not actuated the actuating element 15 within a specified period of time, a message is preferably transmitted to a spatially remote receiver. The receiver outputs this message and a person can initiate a rescue measure.

The actuation of the actuating element 15 is preferably stored together with a time stamp in the gas detection device 100. In one embodiment, the output of a warning and that of an alarm as well as the actuation of the actuating element 15 are stored together with a time stamp in a data memory of the gas detection device 100. Optionally, messages containing these events are also transmitted to the remote receiver and stored there in a data memory.

In the embodiment described so far, the gas detection device 100 is capable of issuing six different messages, namely three different alarms (in the screen areas B.1, B.3 and B.5) and three different warnings (in the screen areas B.2, B.4 and B.6). In one possible embodiment, it can be determined in advance that the gas detection device 100 should only be able to issue some of these six possible messages, but not all of them. The gas detection device 100 can therefore be operated in different modes, whereby each mode determines which of the six possible messages are actually issue at a corresponding target gas concentration.

In one embodiment, the gas detection device 100 comprises an optional first selection switch 16 and an optional second selection switch 17, which can be used to determine the mode in which the gas detection device 100 is currently to be operated. A user can move both selection switches 16, 17 independently of each other to a respective position, see FIG. 1. It is also possible for a service technician to use the input unit 200 to specify in advance the mode in which the gas detection device 100 is currently to be operated. In this implementation, the gas detection device 100 does not necessarily comprise a selection switch 16, 17, and the user cannot generally change the mode.

The modes are explained below using the two selection switches 16 and 17. The first selection switch 16 can be used to determine whether the gas detection device 100 should be able to issue both alarms and warnings or only alarms. FIG. 1 shows a position of the first selection switch 16 which results in both alarms and warnings being issued. The second selection switch 17 can be used to choose between the following four different possible modes:

The gas detection device 100 is capable of issuing an alarm and optionally a warning for both a first aggregated value STEV and a second aggregated value TWA("STEV+TWA"—the position of the second selection switch 17 causes this mode).

The gas detection device 100 is capable of issuing an alarm and optionally a warning for a first aggregated value STEV, but not for a second aggregated value TWA("STEV").

The gas detection device 100 is capable of issuing an alarm and optionally a warning for a second aggregated value TWA, but not for a first aggregated value STEV ("TWA").

The gas detection device 100 is only capable of issuing an alarm and optionally a warning for an instantaneous value, but neither for a first aggregated value STEV nor for a second aggregated value TWA("0").

While specific embodiments of the invention have been shown and described in detail to illustrate the application of the principles of the invention, it will be understood that the invention may be embodied otherwise without departing from such principles.

LIST OF REFERENCE CHARACTERS

| | |
|---|---|
| 1 | Radiation source, emits electromagnetic radiation eS into the measuring chamber 2 |
| 2 | Measuring chamber, holds the gas sample Gp, is penetrated by the electromagnetic radiation eS |
| 3 | Photodetector, generates electrical voltage depending on the intensity of incident electromagnetic radiation eS |
| 4 | Voltage sensor (detection variable sensor), measures the electrical voltage at the output of the photodetector 3 as a detection variable and generates measured values |
| 5 | Housing, accommodates the radiation source 1 inside, the measuring chamber 2, the detector 3, the power supply unit 20, the control unit 9 and the data memory 7, carries the display unit 10 with the screen, the actuating element 15 and the selection switches 16 and 17 |
| 6 | Evaluation unit, receives measured values from the voltage sensor 4, generates the target gas signal from the measured values, derives the target gas concentration from the target gas signal and the functional relationship β, compares the target gas concentration with predefined thresholds and generates alarms and warnings |
| 7 | Data memory in which the functional relationship β between the detection variable and the target gas concentration as well as the upper thresholds and the factor γ are stored |
| 9 | Control unit, controls the output units 10, 11, 12 depending on a signal from the evaluation unit 6 |
| 10 | Screen of a display unit, comprises the six screen areas B.1 to B.6 |
| 11 | Acoustic output unit |
| 12 | Haptic output unit |
| 15 | Actuating element with which a user confirms that they have acknowledged an alarm or warning |
| 16 | First selection switch: only alarms are issued/alarms and warnings are issued |
| 17 | Second selection switch: alarms and warnings are only issued for instantaneous values/for instantaneous values and STEV, but not for TWA/for instantaneous values and for TWA, but not for STEV/for instantaneous values and for STEV and for TWA |
| 20 | Power supply unit |
| 100 | Gas detection device, comprises the sensor unit 1, 2, 3, 4, the output units 10, 11, 12, the control unit 9 with the evaluation unit 6, the data memory 7, the power supply unit 20 and the housing 5 |
| 200 | Remote input unit with which a user specifies values for the upper thresholds $con_{high}$, $TWA_{high}$, $STEV_{high}$ |
| Al | Alarm symbol in screen areas B.1, B.3, B.5 |
| B.1 | Screen area on which the target gas alarm is displayed visually |
| B.2 | Screen area on which the target gas warning is displayed visually |
| B.3 | Screen area on which the first aggregation alarm (STEV) is displayed visually |
| B.4 | Screen area on which the first aggregation warning (STEV) is displayed visually |
| B.5 | Screen area on which the second aggregation alarm (TWA) is displayed visually |
| B.6 | Screen area on which the second aggregation warning (TWA) is displayed visually |
| β | Proportionality factor between the detection variable and the target gas concentration, stored in the data memory 7 |
| $con_{high}$ | Larger target gas threshold, specified with the input unit 200 |
| $con_{low}$ | Smaller target gas threshold |
| γ | Factor between a larger and the corresponding smaller threshold, stored in the data memory 7 |
| Gp | Gas sample in measuring chamber 2 |
| M | Number of sampling points in an operating period, used for TWA |
| N | Number of sampling points for the sliding time window, used for STEV |
| Ö | Opening in the housing of the gas detection device 100, through which the gas sample Gp can enter the measuring chamber 2 |
| S.1 | Symbol for the occurrence of a high target gas concentration in screen areas B.1 and B.2 |
| S.2 | Symbol for the occurrence of a high value for STEV in screen areas B.3 and B.4 |
| S.3 | Symbol for the occurrence of a high value for TWA in screen areas B.5 and B.6 |
| $STEV_{high}$ | Larger aggregation threshold for the aggregation signal STEV, specified with the input unit 200 |
| $STEV_{low}$ | Smaller aggregation threshold for the aggregation signal STEV |
| t(0), t(1), t(2), . . . | Equidistant sampling points |
| t1 | Time at which the STEV signal exceeds the smaller first aggregation threshold $STEV_{low}$ |
| t2 | Time at which the STEV signal exceeds the larger first aggregation threshold $STEV_{high}$ |

-continued

| | |
|---|---|
| t3 | Time at which the signal TWA exceeds the smaller second aggregation threshold $TWA_{low}$ |
| $TWA_{high}$ | Larger aggregation threshold for the aggregation signal TWA, specified with the input unit 200 |
| $TWA_{low}$ | Smaller aggregation threshold for the aggregation signal TWA |
| Wa | Warning symbol in screen areas B.2, B.4, B.6 |
| Z.x | Output area in screen area B.x, in which a numerical value for a target gas concentration is issued (x = 1, . . . , 6) |

What is claimed is:

1. A gas detection device for detecting a target gas or detecting target gases, the gas detection device comprising:
a sensor unit; and
a signal-processing evaluation unit,
wherein the sensor unit is configured to repeatedly measure an indicator of a concentration of the target gas or of at least one of the target gases in a respective gas sample and to generate at least one target gas signal using measured values,
wherein the target gas signal comprises a temporal sequence of target gas signal values,
wherein each target gas signal value refers to a sampling time and comprises the target gas concentration at this sampling time,
wherein the evaluation unit is configured to compare a target gas signal value with a predefined smaller target gas threshold and a predefined larger target gas threshold, if the target gas signal value is between the predefined smaller target gas threshold and the predefined larger target gas threshold, to cause at least one target gas warning to be issued in a form that can be perceived by a human being, and if the target gas signal value is greater than the larger target gas threshold, to cause at least one target gas alarm to be issued in a form that can be perceived by a human being,
wherein the evaluation unit is configured to generate an aggregation signal using the target gas signal,
wherein a signal value of the aggregation signal refers to a reference time which is assigned to a sampling time and includes an aggregated value for the target gas concentration,
wherein the aggregated value is an averaging or accumulation of target gas concentrations at the sampling times of an aggregation time period,
wherein the aggregation time period ends at the reference time to which the aggregated value refers to,
wherein a duration and/or a start of the aggregation time period are specified, and
wherein the evaluation unit is configured to compare an aggregated value with a predefined smaller aggregation threshold and a predefined larger aggregation threshold, if the aggregated value is between the two aggregation thresholds, to cause at least one aggregation warning to be issued in a form that can be perceived by a human being, and if the aggregated value is greater than the larger aggregation threshold, to cause at least one aggregation alarm to be issued in a form that can be perceived by a human being.

2. A gas detection device according to claim 1, wherein the sensor unit comprises a target gas sensor and a detection variable sensor,
wherein the target gas sensor has a detection variable which correlates with the concentration of the target gas or of at least one of the target gases,
wherein the detection variable sensor is configured to repeatedly measure an indicator of the detection variable, and
wherein the sensor unit is configured to use values measured by the detection variable sensor and a predetermined functional relationship between the target gas concentration and the detection variable to generate the target gas signal.

3. A gas detection device according to claim 1,
wherein the aggregation signal is a first aggregation signal, the specified smaller aggregation threshold is a first smaller aggregation threshold, and the specified larger aggregation threshold is a first larger aggregation threshold,
wherein the evaluation unit is configured to generate the first aggregation signal and a second aggregation signal using the target gas signal,
wherein each signal value of the first aggregation signal comprises, as an aggregated value, an averaging of target gas concentrations at the sampling times of a first aggregation time period,
wherein a duration of the first aggregation time period is specified,
wherein each signal value of the second aggregation signal comprises, as an aggregated value, an accumulation of target gas concentrations at the sampling times of a second aggregation time period,
wherein a start of the second aggregation time period is specified,
wherein the evaluation unit is configured to compare an aggregated value of the first aggregation signal with the first smaller aggregation threshold and the first larger aggregation threshold, and to compare an aggregated value of the second aggregation signal with a specified second smaller aggregation threshold and a specified second larger aggregation threshold.

4. A gas detection device according to claim 3, wherein:
the smaller target gas threshold is greater than the first smaller aggregation threshold or the second smaller aggregation threshold, and/or
the larger target gas threshold is greater than the first larger aggregation threshold or the second larger aggregation threshold.

5. A gas detection device according to claim 1, further comprising a visual output unit and a further output unit,
wherein the visual output unit is configured to issue a warning or an alarm in a form that can be visually perceived by a human being,
wherein the further output unit is configured to issue a warning or an alarm in a form that can be perceived acoustically and/or haptically by a human being,
wherein the evaluation unit is configured to, if a target gas signal value lies between the two target gas thresholds and/or an aggregated value lies between the two aggregation thresholds, cause the further output unit to issue a first message as a warning, and if a target gas signal value is greater than the larger target gas threshold and/or an aggregated value is greater than the larger aggregation threshold, cause the further output unit to issue a second message as an alarm, whereby the second message differs from the first message in a manner which can be perceived acoustically and/or haptically.

6. A gas detection device according to claim 1, further comprising an actuating element configured to be actuated by a user of the gas detection device, wherein the gas detection device is configured such that the actuation of the actuating element causes the issuance of the warning to be terminated and the gas detection device is configured such that with the actuation of the actuating element the issuance of an alarm continues.

7. A gas detection device according to claim 1, further comprising an input unit and/or data communication means for an at least temporary data communication with a spatially remote input unit, wherein a factor between 0 and 1 is specified, wherein the input unit is configured to capture a user input for the larger target gas threshold and the or every larger aggregation threshold, and wherein the evaluation unit is configured to use as the smaller target gas threshold a product of the factor and the captured larger target gas threshold and to use as the or every smaller aggregation threshold a product of the factor and the respective captured larger aggregation threshold.

8. A gas detection device according to claim 1, wherein the gas detection device is configured to be operated in one of at least two different possible modes, wherein in a first one of the at least two different possible modes, the gas detection device is only capable of issuing a target gas alarm and a target gas warning, but not an aggregation alarm or an aggregation warning, and wherein, in a second one of the at least two different possible modes, the gas detection device is capable of issuing both a target gas alarm and a target gas warning and both a an aggregation alarm and an aggregation warning.

9. A gas detection device according to claim 1, wherein the aggregation signal is a first aggregation signal, and the evaluation unit is configured to generate the first aggregation signal and a second aggregation signal being different from the first aggregation signal by using the target gas signal, wherein the gas detection device is configured to be operated in one of at least three different possible aggregation modes, wherein in a first one of the at least three different possible aggregation modes the gas detection device is configured to issue an aggregation alarm and an aggregation warning depending on both the first aggregation signal and the second aggregation signal, wherein in a second one of the at least three different possible aggregation modes the gas detection device is configured to issue an aggregation alarm and an aggregation warning depending on the first aggregation signal, but not depending on the second aggregation signal, and wherein in a third one of the at least three different possible aggregation modes the gas detection device is configured to issue an aggregation alarm and an aggregation warning depending on the second aggregation signal, but not depending on the first aggregation signal.

10. A gas detection process for detecting a target gas or detecting target gases using a gas detection device comprising a sensor unit and a signal-processing evaluation unit, the process comprising the steps of:

with the sensor unit, repeatedly measuring an indicator of a concentration of the target gas or of at least one of the target gases in a respective gas sample; and with the sensor unit, generating a target gas signal for each target gas using measured values, wherein the target gas signal comprises a temporal sequence of target gas signal values, wherein each target gas signal value refers to a sampling time and comprises the target gas concentration at this sampling time, with the evaluation unit, comparing a target gas signal value with a predefined smaller target gas threshold and a predefined larger target gas threshold, and upon the target gas signal value being between the smaller target gas threshold and the larger target gas threshold, causing a target gas warning to be issued in at least one form that can be perceived by a human being, and if the target gas signal value is greater than the larger target gas threshold, causing a target gas alarm to be issued in at least one form that can be perceived by a human being, with the evaluation unit, generating an aggregation signal using the target gas signal, wherein the aggregation signal refers to a reference time which is assigned to a sampling time and includes an aggregated value for the target gas concentration, wherein the aggregated value is an averaging or accumulation of target gas concentrations at the sampling times of an aggregation time period, wherein the aggregation time period ends at the reference time to which the aggregated value refers, wherein a duration and/or a start of the aggregation time period are specified; and with the evaluation unit, comparing an aggregated value with a predefined smaller aggregation threshold and a predefined larger aggregation threshold and if the aggregated value lies between the smaller aggregation threshold and the larger aggregation threshold, causing an aggregation warning to be issued in a form that can be perceived by a human being, and if the aggregated value is greater than the larger aggregation threshold, causing an aggregation alarm to be issued in a form that can be perceived by a human being.

* * * * *